(12) United States Patent
Tian et al.

(10) Patent No.: US 10,856,818 B2
(45) Date of Patent: Dec. 8, 2020

(54) SYSTEMS AND METHODS FOR ESTIMATING IRRADIATION DOSE FOR PATIENT APPLICATION BASED ON A RADIATION FIELD MODEL AND A PATIENT ANATOMY MODEL

(71) Applicant: Duke University, Durham, NC (US)

(72) Inventors: Xiaoyu Tian, Durham, NC (US); Ehsan Samei, Durham, NC (US); Paul Segars, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/531,730

(22) Filed: Aug. 5, 2019

(65) Prior Publication Data
US 2020/0060631 A1 Feb. 27, 2020

Related U.S. Application Data

(63) Continuation of application No. 15/283,708, filed on Oct. 3, 2016, now Pat. No. 10,463,317.

(60) Provisional application No. 62/235,659, filed on Oct. 1, 2015.

(51) Int. Cl.
*A61B 6/00* (2006.01)
*A61B 6/03* (2006.01)
*G16H 50/50* (2018.01)

(52) U.S. Cl.
CPC ............... *A61B 6/032* (2013.01); *A61B 6/50* (2013.01); *A61B 6/544* (2013.01); *A61B 6/545* (2013.01); *G16H 50/50* (2018.01)

(58) Field of Classification Search
CPC .......... G16H 50/50; A61B 6/032; A61B 6/50; A61B 6/544; A61B 6/545
See application file for complete search history.

(56) References Cited

U.S. PATENT DOCUMENTS

2015/0100290 A1\* 4/2015 Falt ..................... G16B 5/00
703/2

OTHER PUBLICATIONS

Non-Final Office Action issued in counterpart U.S. Appl. No. 15/283,708 dated May 30, 2019.
Notice of Allowance issued in counterpart U.S. Appl. No. 15/283,708 dated Jun. 27, 2019.
Response to Non-Final Office Action issued in counterpart U.S. Appl. No. 15/283,708 dated Jun. 6, 2019.

\* cited by examiner

*Primary Examiner* — Dani Fox
(74) *Attorney, Agent, or Firm* — Olive Law Group, PLLC

(57) ABSTRACT

Systems and methods for estimating irradiation dose for patient application based on a radiation field model and a patient anatomy model are disclosed. According to an aspect, a method includes providing a database of patient anatomy models. The method also includes providing a radiation field model of an X-ray system. Further, the method includes receiving a measure of an anatomy of a patient. The method also includes determining a patient anatomy model among the patient anatomy models that matches or is similar to the anatomy of the patient based on the measure of the patient and a corresponding measure of each of the patient anatomy models. The method also includes estimating an irradiation dose for application to the patient by the X-ray system based on the radiation field model and the determined patient anatomy model.

18 Claims, 8 Drawing Sheets

SYSTEMS AND METHODS FOR ESTIMATING IRRADIATION DOSE FOR PATIENT APPLICATION BASED ON A RADIATION FIELD MODEL AND A PATIENT ANATOMY MODEL

CROSS REFERENCE TO RELATED APPLICATION

This application claims the benefit of and is a continuation of U.S. patent application Ser. No. 15/283,708 filed Oct. 3, 2016, which claims priority to U.S. Provisional Patent Application 62/235,659, filed Oct. 1, 2015, and titled SYSTEMS AND METHODS FOR ESTIMATING IRRADIATION DOSE FOR PATIENT APPLICATION BASED ON A RADIATION FIELD MODEL AND A PATIENT ANATOMY MODEL, the contents of which are incorporated herein by reference in their entireties.

FEDERALLY SPONSORED RESEARCH OR DEVELOPMENT

This invention was made with government support under grant R01 EB001838 awarded by National Institutes of Health (NIH). The government has certain rights to the invention.

TECHNICAL FIELD

The present disclosure relates to imaging. More particularly, the present disclosure relates to estimation of irradiation dose for patient application based on a radiation field model and a patient anatomy model.

BACKGROUND

A computed tomography (CT) scan makes use of computer-processed combinations of X-ray images captured from different angles to produce cross-sectional (tomographic) images of specific areas of a scanned object. Medical imaging is a common application of X-ray CT. Its cross-sectional images are used for diagnostic and therapeutic purposes in various medical disciplines for patient care.

Reduction of radiation dose during CT examinations without compromising image quality is an important issue. Generally, higher radiation doses result in higher-resolution images, while lower doses lead to increased image noise and artifactual images. However, increased dosage can increase the risk of adverse side effects, including the risk of radiation induced cancer. Several approaches have been used to reduce radiation exposure during CT examinations. However, there is a continuing need to provide improved systems and techniques for accurately determining and subsequently optimizing (i.e., reducing) patient radiation dose during CT examinations while also obtaining high-quality CT images.

SUMMARY

Disclosed herein are systems and methods for estimating irradiation dose for patient application based on a radiation field model and a patient anatomy model. According to an aspect, a method includes providing a database of patient anatomy models. The method also includes providing a radiation field model of an X-ray system. Further, the method includes receiving a measure of an anatomy of a patient. The method also includes determining a patient anatomy model among the patient anatomy models that matches or is similar to the anatomy of the patient based on the measure of the patient and a corresponding measure of each of the patient anatomy models. The method also includes estimating an irradiation dose for application to the patient by the X-ray system based on the radiation field model and the determined patient anatomy model.

BRIEF DESCRIPTION OF THE DRAWINGS

The summary above, as well as the following detailed description of illustrative embodiments, is better understood when read in conjunction with the appended drawings. For the purpose of illustrating the present disclosure, example constructions of the disclosure are shown in the drawings. However, the present disclosure is not limited to specific methods and instrumentalities disclosed herein. Moreover, those in the art will understand that the drawings are not to scale or reflect exact mathematical dependencies. Wherever possible, like elements have been indicated by identical numbers.

Embodiments of the present disclosure will now be described, by way of example only, with reference to the following diagrams in which.

DETAILED DESCRIPTION

The following detailed description illustrates embodiments of the present disclosure and manners by which they can be implemented.

The example functions and methods disclosed herein may be implemented by any suitable X-ray system, such as a CT imaging system. A CT imaging system may use a three-dimensional (3D) rotational X-ray examination device having one or more X-ray tubes and the same number of detectors placed on a gantry that is rotated around a patient. Other types of CT imaging systems may use 3D examination devices equipped with a stationary detector ring with multiple pixels that is mounted on the stator of the gantry, and only the X-ray tube is rotating with the rotor of the gantry around the patient. The CT scanning may be based on a rectilinear propagation and attenuation of X-rays. The CT imaging system may thereby acquire a series of X-ray projections from a range of angles around the subject. Each projection can represent the value (or collection of values in a multi-element X-ray detector) of the X-ray attenuation line integral through the object along the line from an X-ray source to an X-ray detector. Imaging an object to be graphically reconstructed at equiangular-spaced views over 180° forms a complete set of projection data. Tomographic image reconstruction can create a two-dimensional (2D) image (or 3D volume) from the measured projection data.

As a fundamental step to manage and optimize radiation dose, it is important to quantify patient-specific organ dose. Such dose estimates can provide information useful for the design of individualized CT protocols, for the assessment and improvement of patient imaging management decisions, and for optimizing CT dose in relationship with image quality of the study.

For the purposes herein, a patient may be defined as a human being of any age, gender, body habitus, and/or pregnancy status. For the avoidance of doubt, a patient may be, but is not limited to, a child, an adult, or a pregnant woman.

Figure 1:
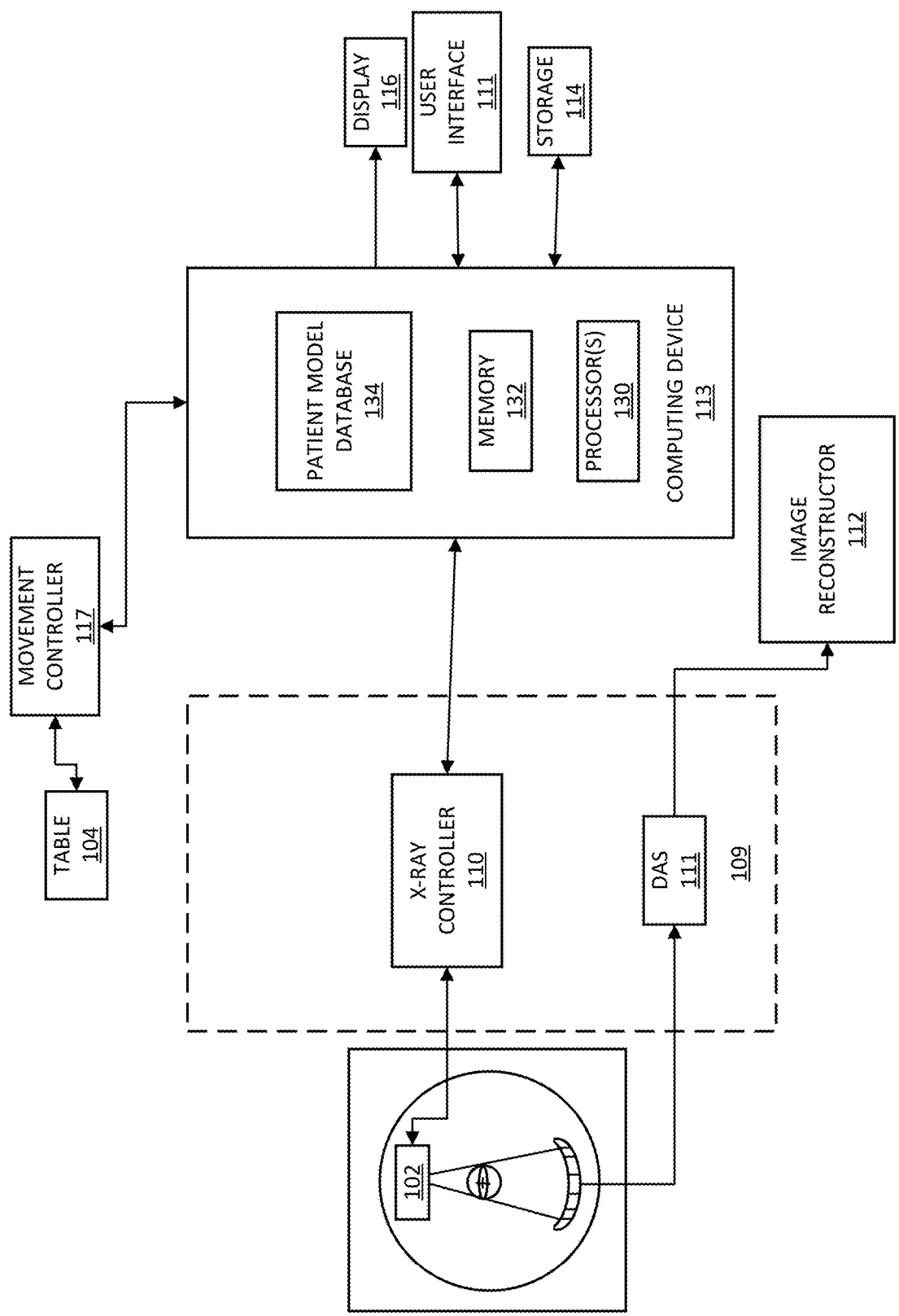
FIG. 1 is a schematic diagram of a CT imaging system for estimating irradiation dose for patient application based on a radiation field model and a patient anatomy model in accordance with embodiments of the present disclosure.

FIG. 1 illustrates a schematic diagram of a CT imaging system 100 for estimating irradiation dose for patient application based on a radiation field model and a patient anatomy model in accordance with embodiments of the present disclosure. Referring to FIG. 1, the system 100 includes a rotational gantry 101 that is rotatable about a longitudinal axis 108 of a patient's body 107 or any other object to be examined. The gantry 101 may include one or more X-ray sources or tubes 102 that are configured to project a beam of X-rays 106 towards an X-ray detector array 103 placed at the opposite side of the gantry 101. The X-ray detector array 103 can be equipped with multiple detector elements 103a which can together sense the projected X-rays passing through the patient's body 107 to be examined between X-ray detector array 103 and X-ray source 102. Each detector element 103a can generate an electrical signal that represents the intensity of an impinging X-ray beam and can hence be used to estimate the attenuation of the beam as it passes through the object.

In a rotational CT scanner such as depicted in FIG. 1, a 3D volume can be calculated by reconstructing and stacking individual 2D slices. Some CT imaging systems can employ 2D detector arrays, allowing the acquisition of truly 3D data sets. In this particular example, only a single row of detector elements 103a is shown (i.e., a detector row). However, a multi-slice detector array such as denoted by reference number 103 include multiple parallel rows of detector elements 103a such that projection data corresponding to multiple quasi-parallel or parallel slices can be acquired simultaneously during a scan. The detector elements 103a may completely encircle the patient 107. This figure shows only a single X-ray source 102, but it should be understood that multiple X-ray sources may be positioned around gantry 101.

Operation of X-ray source 102 can be governed by a control mechanism 109 of the system 100. Control mechanism 109 can include an X-ray controller 110 that provides power and timing signals to one or more X-ray sources 102. A data acquisition system (DAX) 111 belonging to the control mechanism 109 can sample analog data from detector elements 103a and can convert the data to digital signals for subsequent processing. An image reconstructor 112 can receive sampled and digitized X-ray data from DAS 111 and can perform high-speed image reconstruction. The reconstructed image can be applied as an input to a computing device 113 (e.g., a desktop or laptop computer), which stores the image in a mass storage device 114. The computing device 113 may include hardware, software, firmware, or combinations thereof for implementing the functionality described herein. For example, the computing device 113 may include one or more processors 130 and memory 132. The image reconstructor 112 may be specialized hardware residing in the computing device 113 or a software program executed by the computing device 113.

The computing device 113 may receive signals via a user interface or graphical user interface (GUI). Particularly, the computing device 113 may receive commands and scanning parameters from a user interface 115 that includes, for example, a keyboard and mouse (not shown). An associated display 116 can allow an operator to observe the reconstructed image and other data from the computing device 113. The operator-supplied commands and parameters can be used by the computing device 113 to provide control signals and information to the X-ray controller 110, DAX 111, and a table motor controller 117 in communication with a patient table 104, which controls a motorized patient table 104 so as to position patient 107 in gantry 101. Particularly, the patient table 104 can move the patient 107 through a gantry opening.

Figure 2:
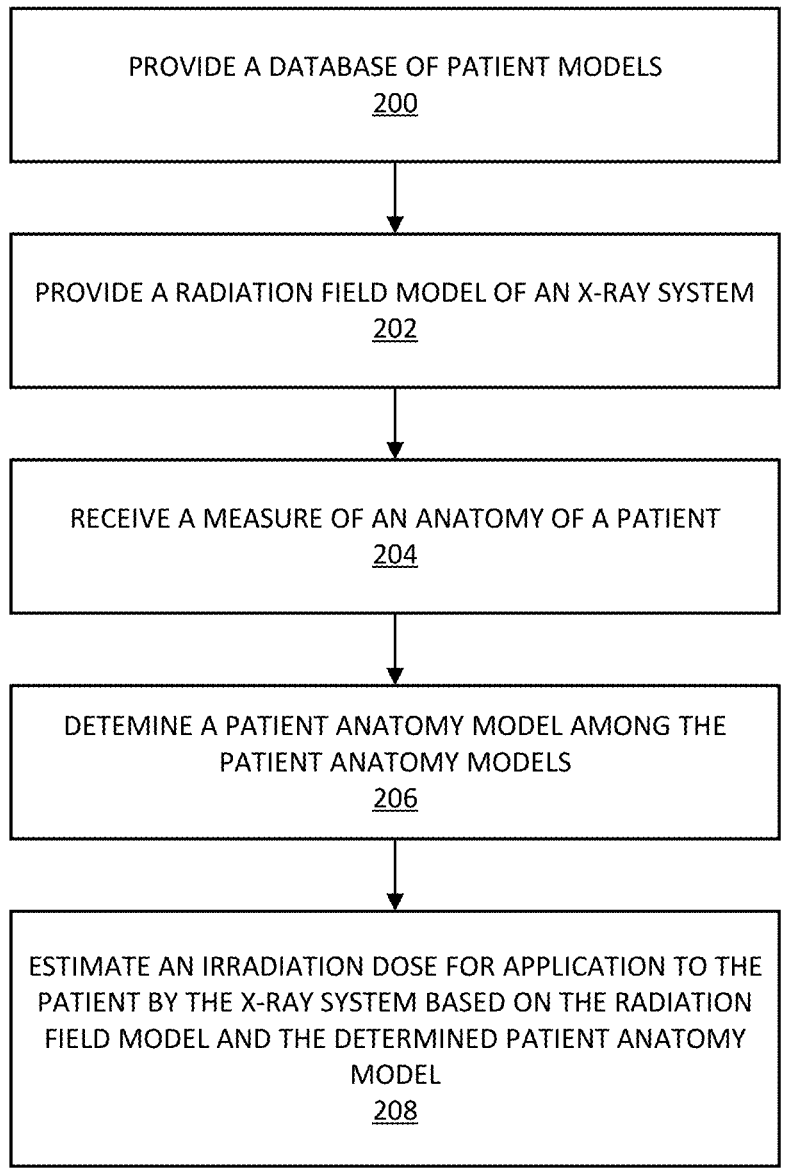
FIG. 2 is a flowchart of an example method for estimating irradiation dose for patient application based on a radiation field model and a patient anatomy model in accordance with embodiments of the present disclosure.

The computing device 113 or another suitable computing device may be configured to implement the functionality described herein. More particularly, for example, FIG. 2 illustrates a flowchart of an example method for estimating irradiation dose for patient application based on a radiation field model and a patient anatomy model in accordance with embodiments of the present disclosure. Referring to FIG. 2, the memory 132 may include suitable instructions executable by the processor(s) 130 for implementing the functionality described herein.

The method of FIG. 2 includes providing 200 a database of patient models. Referring to FIG. 1 for example, the computing device 113 may include a database 134 of patient models residing in its memory 132 or may have access to memory that stores the database 134. The patient anatomy models may include patient anatomy models of differing ages, sizes, genders, and/or other characteristics of an individual. To model the patient anatomy, the database 134 may have a library of computational phantoms with representative ages, sizes, genders, and/or other characteristics of an individual. The large number of unique models in the library aims to reflect the anatomical variability across a population.

Figure 3:
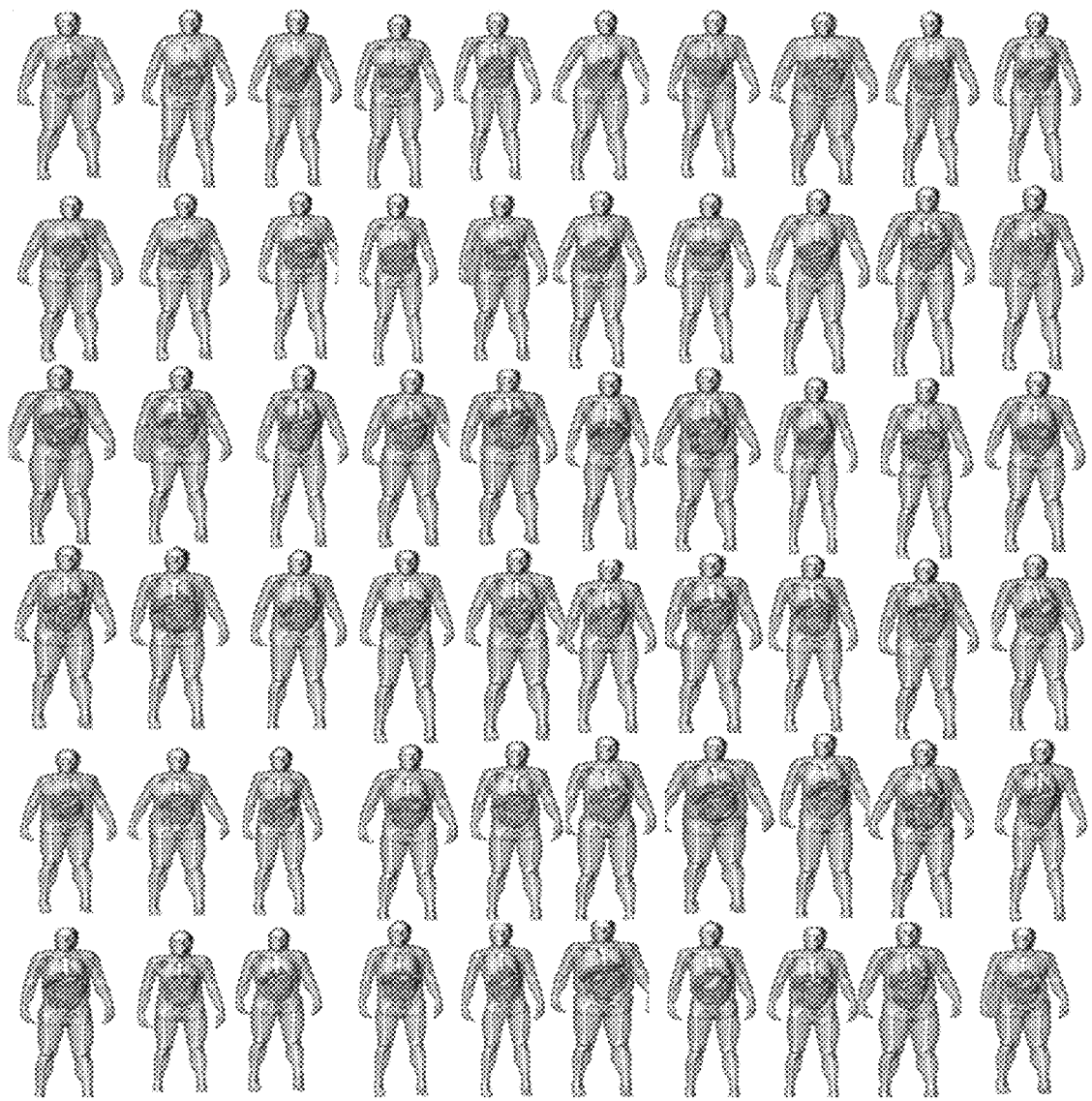
FIG. 3 are images of three-dimensional (3D) frontal views of example patient models used in a study (arms can be raised or lowered for simulation of body scans)

An initial model may be first created by segmenting bones and major organs within a CT image volume. A 3D surface may subsequently be fit to polygon models using non-uniform rational B-splines (NURBS) modeling software (such as the modeling software available from Rhinoceros, McNeel North America, of Seattle, Wash.). Other organs and structures may be defined by morphing structures from existing male or female full body adult and pediatric models. Volumes of the morphed organs/structures may be checked and scaled, if desired or needed, to match age-interpolated organ volume and anthropometry data. The full-body patient models may include most of the radiosensitive organs as understood by those of skill in the art and can be incorporated into simulation programs for image quality or dose estimation. FIG. 3 illustrates images of 3D frontal views of example patient models used in a study with all arms being raised for simulation of body scans.

The method of FIG. 2 includes providing 202 a radiation field model of an X-ray system. Continuing the aforementioned example, the system 100 may store in its memory 132 or have access to memory that stores a radiation field model of the X-ray source 102. In an example, each radiation field model may be a computational model that is generated based on a clinical CT case.

In an example, a radiation field model can be generated by detailed modeling of one or more geometries of the X-ray system, X-ray tube motion of the X-ray system, a characteristic of a bowtie filter of the X-ray system, peak kilovoltage (kVp) of the X-ray system, and a peak milliampere (mA) of the X-ray system. The model can effectively quantify the heterogeneous dose field created by the change of tube current.

Organ dose under fixed tube current may be simulated using a validated Monte Carlo simulation program as the estimation basis. Such organ dose values may be normalized by CTDIvol and modeled as a function of patient size to derive the so-called $h_{organ}$. $h_{organ}$ can be regarded as a factor that relates the organ dose values to patient anatomy under a unified dose field (constant tube current condition). It may be used as the basis for estimating organ dose under an arbitrary dose field depending on the detailed TCM profile.

An organ-specific $CTDI_{vol}$ may be further generated to account for the heterogeneous distribution of the dose field under TCM schemes. The dose field modeling needs to effectively quantify the heterogeneous distribution created by dynamic tube current changes.

Initially, the dose rate profile of a thin beam (for example, 25-mm full-width at half-maximum) may be generated by Monte Carlo simulation, depicting the z-dimensional dose distribution for an infinitely long fixed or variable-sized phantom. Subsequently, the dose rate profile may be convolved with TCM and constant tube current profiles to generate the accumulated z-dimensional dose distributions under each condition. The difference between the accumulated dose distributions under TCM and constant tube current conditions may be determined and overlaid with the patient organ distribution. Based on this information, a regional $CTDI_{vol}$ value can be calculated for each organ to account for the local dose field.

Now returning to FIG. 2, the method includes receiving 204 a measure of an anatomy of a patient. Continuing the aforementioned example of FIG. 1, the computing device 113 can receive a measure of an anatomy of a patient. The computing device 113 may receive, for example, a measure of a distance between the base of the neck through the bottom of the pelvois (i.e., the normal range of a standard chest, abdomen and pelvis CT). For example, with an atlas of computational phantoms that cover a broad range of human anatomy, a new clinical patient can be matched to a corresponding model that closely resembles the patient in terms of major organ locations. The patient trunk height, defined as the distance between the top of clavicle to the end of the pelvic region, may be measured from the topogram image of the patient and matched against XCAT phantoms in the library.

The method of FIG. 2 includes determining 206 a patient anatomy model among the patient anatomy models that matches or is similar to the anatomy of the patient based on the measure of the patient and a corresponding measure of each of the patient anatomy models. As an example, a patient anatomy model among the patient anatomy models may be determined based on a comparison of a measure of the distance between the top of the clavicle and the end of the pelvic region in the anatomy models. Particularly, for example, the computing device 113 can receive or determine a distance between the top of the clavicle and the end of the pelvic region of the patient. This distance may be an exact, substantially close, or approximation. In addition, the computing device 113 can receive or determine the distance between the top of the clavicle and the end of the pelvic region in each of multiple patient anatomy models. The distance for the patient may be compared to the models to determine one or more models that closely or exactly match the distance for the patient. It should be noted that any suitable measure or measures may be utilized for matching a patient to one or more similar anatomy models for use in accordance with the present disclosure.

Figure 4:
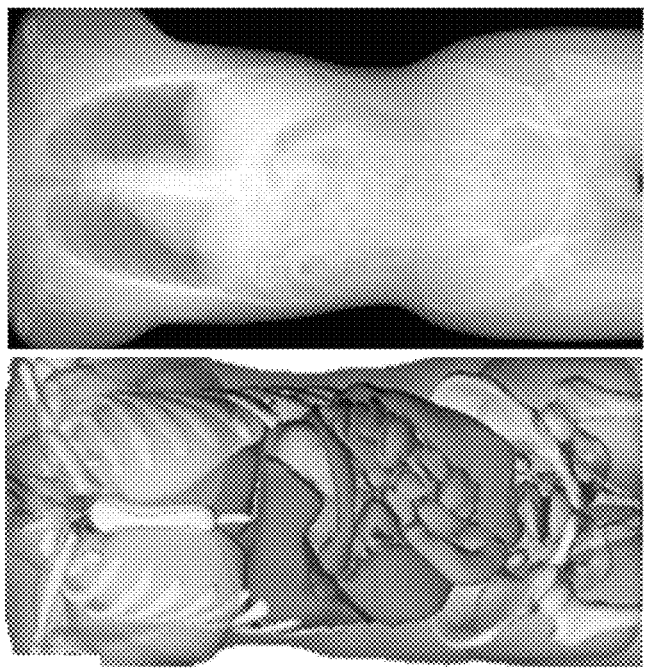
FIG. 4 depicts an image illustrating two pairs of matched models.
Figure 4:
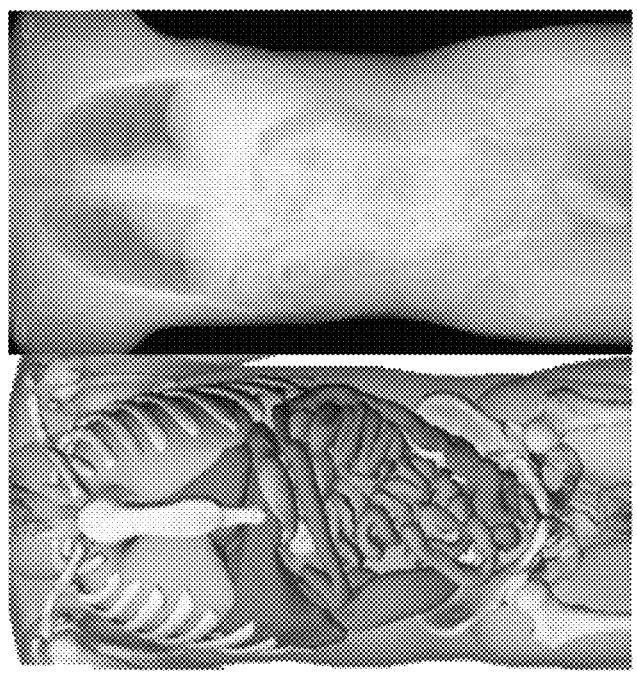

FIG. 4 depicts an image illustrating two pairs of matched models (male and female patients at 50% height and weight). As shown at reference (a) of FIG. 4, an example patient-model matching pair as determined by trunk height for the 50th percentile male is depicted. As shown at reference (b) of FIG. 4, an example patient-model matching pair as determined by trunk height for the $50^{th}$ percentile female is depicted.

Figure 5:
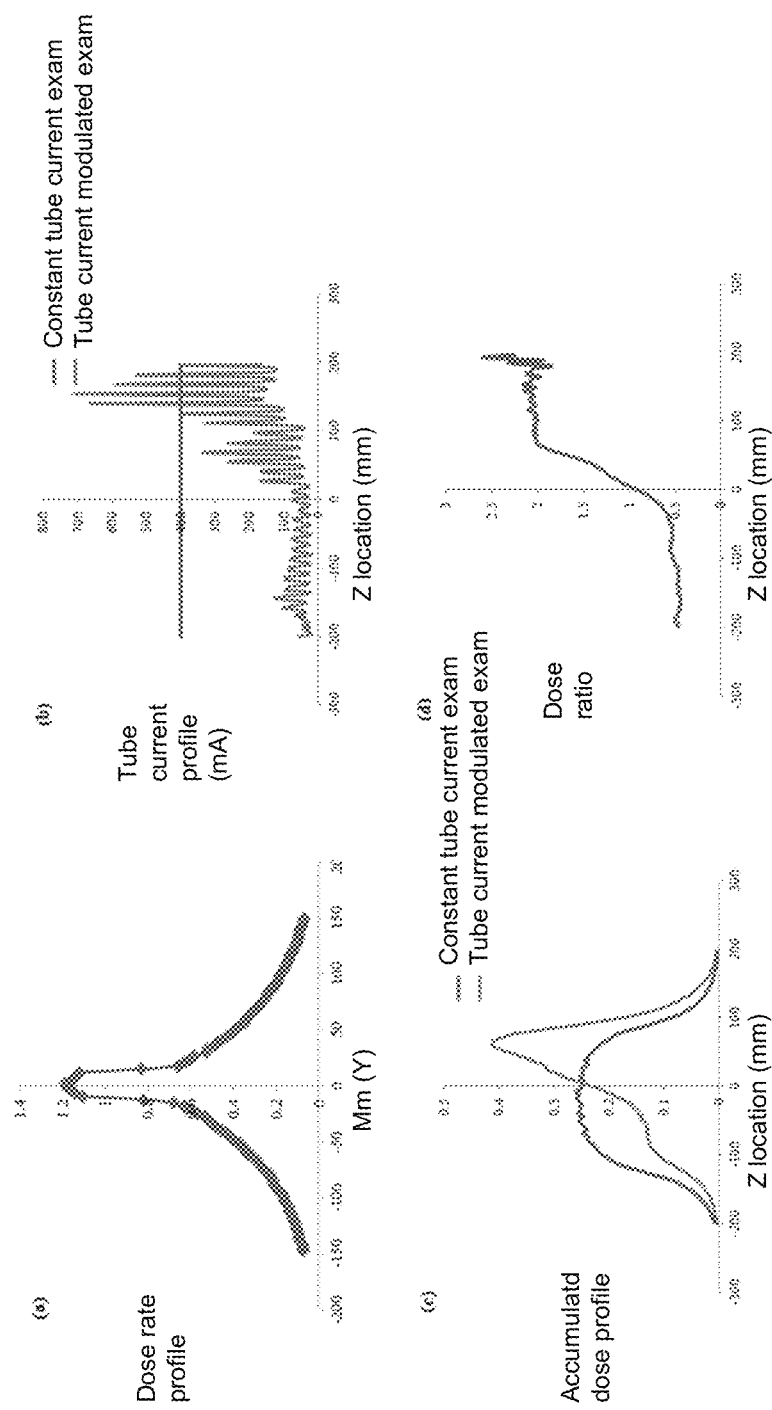
FIG. 5 is a graph showing the dose rate profile over an infinitely long CTDI phantom for a thin beam (25 mm full width at half maximum) generated by Monte Carlo simulation, example tube current profiles of TCM and constant tube current scans, a Z dimensional accumulated dose profile for TCM and a constant tube current scan derived by convolving the dose rate profile with tube current profiles, and the dose ratio derived by dividing the accumulated dose profile of a TCM scan by a constant tube current scan.

As shown in FIG. 5, reference character (a) of FIG. 5 illustrates a graph showing the dose rate profile over an infinitely long CTDI phantom for a thin beam (25 mm full width at half maximum) generated by Monte Carlo simulation. Reference character (b) of FIG. 5 illustrates a graph showing example tube current profiles of TCM and constant tube current scans. Reference character (c) of FIG. 5 illustrates a graph showing a Z dimensional accumulated dose profile for TCM and a constant tube current scan derived by convolving the dose rate profile with tube current profiles. Reference character (d) of FIG. 5 illustrates a graph showing the dose ratio derived by dividing the accumulated dose profile of the TCM scan by the constant tube current scan.

The organ-specific $CTDI_{vol}$ factor may be computed as $$(CTDI_{vol})_{organ,convolution} = R_{organ} CTDI_{vol}, \quad (1)$$

$$R_{organ} = \frac{\sum_{z \in \{organ\}} \text{Dose ratio}_z * N_z}{\sum_{z \in \{organ\}} N_z}, \quad (2)$$

where $CTDI_{vol}$ refers to the $CTDI_{vol}$ reported on the CT scanner console, which is derived using the average mAs of the CT exam. $R_{organ}$ represents the dose field difference between the specific TCM exam and the constant mAs condition. Dose ratio$_z$ is the dose ratio value at location z, and N is the number of organ voxels in the axial slice at location z. Such organ-specific $CTDI_{vol}$ can be regarded as a regional $CTDI_{vol}$ that reflects the difference of the strength of the dose field between TCM and constant mAs for a specific organ. It is used as an adjustment factor to account for the regional dose field.

The method of FIG. 2 includes estimating 208 an irradiation dose for application to the patient by the X-ray system based on the radiation field model and the determined patient anatomy model. Continuing the aforementioned example, the computing device 113 may estimate an irradiation dose for application to the patient by the X-ray system based on the radiation field model and the determined patient anatomy model.

With effective methods to approximate the patient anatomy and radiation field, dose to each organ of a patient undergoing a CT examination with TCM, $H_{organ}$, can be estimated as $$H_{TCM} = h_{organ} * (CTDI_{vol})_{organ, convolution}. \quad (3)$$

Figure 6:
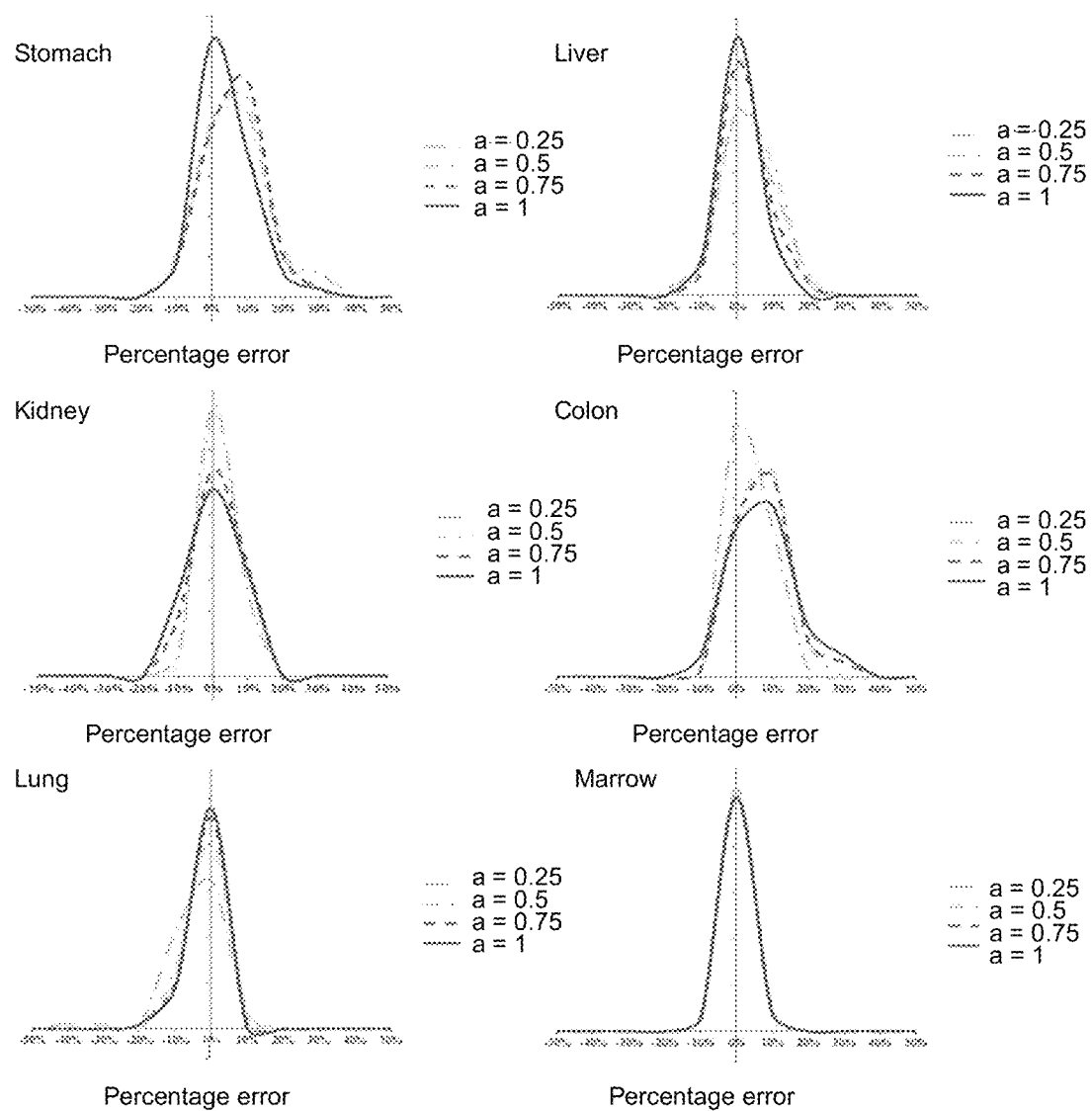
FIG. 6 are graphs showing a histogram of error in predicting organ dose for the abdominopelvic scans.

In a study, the accuracy of the proposed estimation methods may be evaluated by incorporating tube current modulation into the Monte Carlo program and estimating the organ dose across the 58 patient models as the gold standard. As noted earlier, each patient case can be matched to an XCAT model based on trunk height. The organ dose can subsequently be estimated using the proposed patient matching and convolution method under five modulation strengths. The gold standard for the comparison was the organ dose for the original phantom with TCM explicitly modeled in the MC simulation. The accuracy of abdominopelvic exam in one case is shown in FIG. 6, which illustrates graphs showing a histogram of error in predicting organ dose for the abdominopelvic scans. In FIG. 6, the x-axis is determined as the difference between the estimated and actual organ doses normalized by the $CTDI_{vol}$ of the exam.

Figure 7:
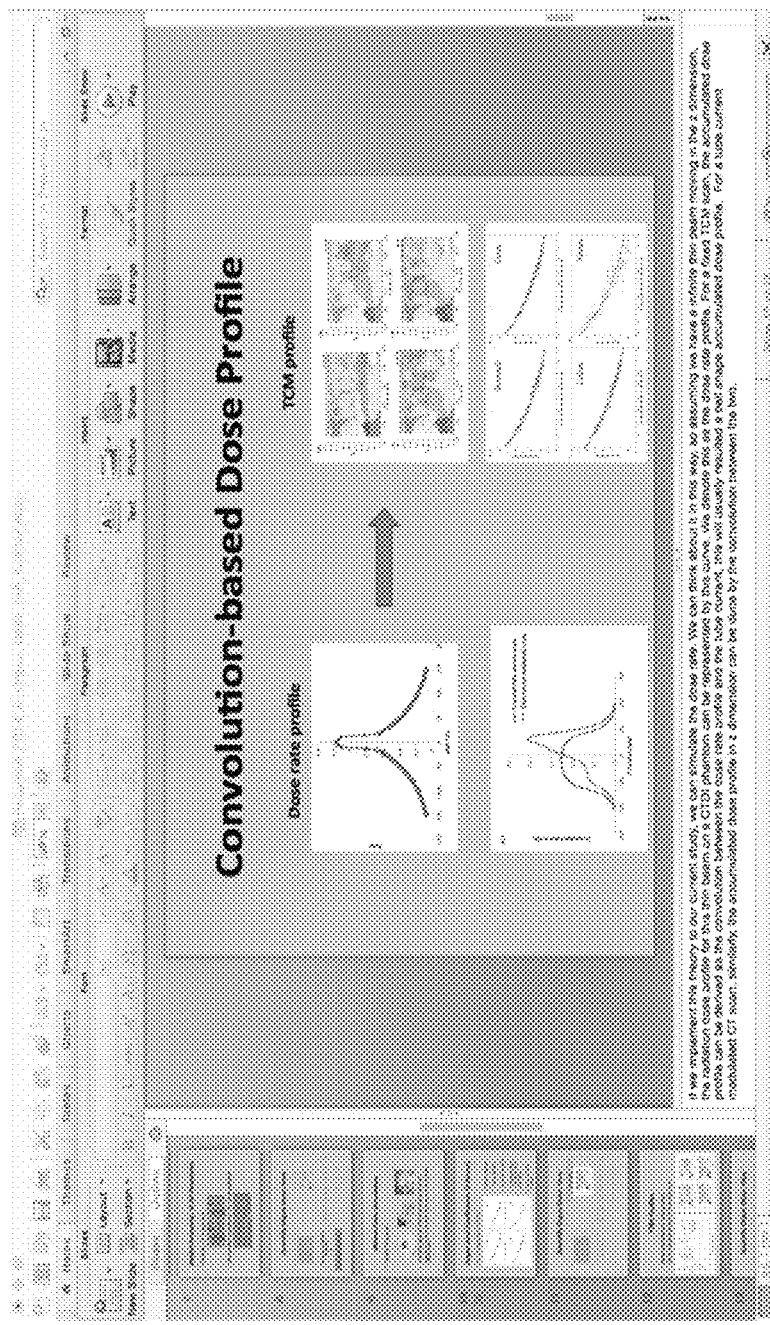
FIG. 7 is a screen display of an example progress report showing a written record in accordance with embodiments of the present disclosure.

FIG. 7 illustrates a screen display of an example progress report showing a written record in accordance with embodiments of the present disclosure.

As discussed, prediction and estimation of quality and safety aspects of an imaging exam can require a priori knowledge of internal geometrical attributes or characteristics of a patient. For example, a computing device may use organ location, size, dimension, and the like. This information or data can be used to match the patient to one or more anatomy or virtual models of humans through various suitable techniques. In an example, a patient may be matched to one or more models based on patient height, weight, gender, body mass index (BMI), racial profile, the like, or combinations thereof. In another example, a patient may be matched to one or more models based on a cross correlation of single- or multiple-view "scout" (2D) images to like synthetic images from virtual models. In other examples, a patient may be matched based on measured (automatically or manually from 2D or 3D data) patient's chest-height, abdomen-height, and abdominopelvic-height or such to like closest values from virtual models. In other example, a patient may be matched based on use of deep learning techniques based on prior manually-matched models for devising a stochastic predictive matching model. Further, any of these techniques, example, or combinations thereof may be utilized.

In accordance with embodiments, a computing device, such as computing device 113 shown in FIG. 1, may suitably determine and present to a user the accuracy of predictions derived based on matching of the patient to the models. The accuracy may be based on a measured closeness of the match or matches. For example, for a given match for an actual patient, a quantification of the match may be determined based on geometrical properties. Match success can be combined into scalar metric of match fidelity. The match fidelity may be related to uncertainty in organ dose estimation. Uncertainty in organ dose estimation (confidence intervals) can be ascribed to predicted organ dose values.

Figure 8:
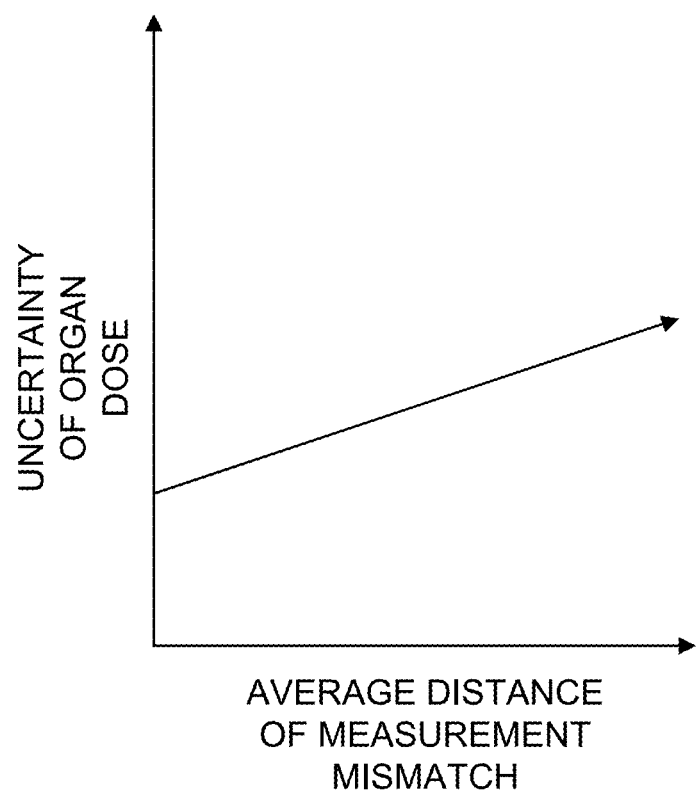
FIG. 8 illustrates a graph showing an example relationship of the uncertainty of organ dose estimation to an average distance of measurement mismatch between an actual patient and matched models.

FIG. 8 illustrates a graph showing an example relationship of the uncertainty of organ dose estimation to an average distance of measurement mismatch between an actual patient and matched models. While the example shown is linear, this relationship is expected to take a non-linear form that is further a function of the organ and the imaging protocol used.

It is noted that once a patient is matched to virtual or anatomy models, additional undertakings may involve derivation of organ dose, image quality values, diagnostic quality, and other such image or patient related attributes. This can be based on rapid calculation or look up tables associated with the virtual models undergoing similar procedures as that for the patient.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the presently disclosed subject matter. In the case of program code execution on programmable computers, the computer will generally include a processor, a storage medium readable by the processor (including volatile and non-volatile memory and/or storage elements), at least one input device and at least one output device. One or more programs may be implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

While various embodiments of the present disclosure have been illustrated and described, it will be clear that the present disclosure is not limited to these embodiments only. Numerous modifications, changes, variations, substitutions, and equivalents will be apparent to those skilled in the art, without departing from the spirit and scope of the present disclosure. The singular forms "a," "an," and "the" include plural referents unless the context clearly dictates otherwise. Unless otherwise indicated, all numbers expressing quantities of distance, frequencies, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

The invention claimed is:

1. A method comprising:
providing a database of patient anatomy models;
providing a radiation field model of an X-ray system;
determining an X-ray distribution created by dynamic tube current changes of the X-ray system to generate the radiation field model;
receiving a measure of an anatomy of a patient;
determining a patient anatomy model among the patient anatomy models that matches or is similar to the anatomy of the patient based on the measure of the patient and a corresponding measure of each of the patient anatomy models; and
estimating an irradiation dose for application to the patient by the X-ray system based on the radiation field model and the determined patient anatomy model, and
wherein determining an X-ray distribution comprises:
determining a dose rate profile based on Monte Carlo simulation;
convolving the dose rate profile with tube current modulation (TCM) and constant tube profiles to generate accumulated z-dimensional dose distributions for each condition;
determining accumulated dose distributions under TCM and constant tube current conditions;
overlaying the accumulated dose distributions with patient organ distributions identified in the patient anatomy models;
determining a regional dose index for organs to account for a local dose field; and
multiplying the dose index with volume computed tomography dose index ($CTDI_{vol}$)-normalized organ dose coefficients under constant tube current to approximate organ dose for TCM computed tomography examination.

2. The method of claim 1, wherein the database of patient anatomy models includes patient anatomy models of differing ages, sizes, and genders.

3. The method of claim 1, further comprising:
receiving image data of a plurality of patients;
identifying internal structures of the patients based on the image data; and
generating the patient anatomy models based on the identified internal structures.

4. The method of claim 3, wherein the image data is computed tomography (CT) image data.

5. The method of claim 3, wherein identifying internal structures comprises segmenting bones and organs within an image volume of the image data.

6. The method of claim 3 further comprising morphing structures from other patient anatomy models to identify other internal structures, and wherein generating the patient anatomy models comprises using the identified other internal structures to generate the patient anatomy models.

7. The method of claim 1, further comprising:
applying automated segmentation and anatomical benchmarks on a topogram image of the patient;
registering the anatomical benchmarks and the major organs against the patient anatomy models; and
auto-correlating between the topogram image of the patient and the patient anatomy models.

8. The method of claim 1, wherein receiving a measure of an anatomy of a patient comprises receiving a measure of a distance between a clavicle of the patient to a pelvic region of the patient.

9. The method of claim 8, wherein the measure of the distance is a distance between the top of the clavicle and an end of the pelvic region.

10. The method of claim 1, further comprising:
receiving a tomogram image of the patient; and
determining the measure of the anatomy of the patient based on the tomogram image.

11. The method of claim 10, wherein the database of patient anatomy models includes extended cardiac-torso (XCAT) phantoms or similar patient models, and
wherein determining a patient anatomy model comprises determining the patient anatomy model among the patient anatomy models that matches or is similar to the anatomy of the patient based on the distance between the top of the clavicle and the end of the pelvic region in the tomogram image as compared to the corresponding measure in the XCAT phantoms or similar anatomical models.

12. The method of claim 1, wherein the radiation model comprises at least one of a geometry of the X-ray system, X-ray tube motion of the X-ray system, a characteristic of a bowtie filter of the X-ray system, peak kilovoltage (kVp) of the X-ray system, and a peak milliampere (mA) of the X-ray system.

13. The method of claim 1, wherein the X-ray system comprises a computed tomography imaging system.

14. The method of claim 1, wherein estimating the irradiation dose comprises estimating the irradiation does of the patient undergoing computed tomography examination.

15. A system comprising:
at least one computing device including at least one processor and memory configured to:
provide a database of patient anatomy models;
provide a radiation field model of an X-ray system;
determine an X-ray distribution created by dynamic tube current changes of the X-ray system to generate the radiation field model;
receive a measure of an anatomy of a patient;
determine a patient anatomy model among the patient anatomy models that matches or is similar to the anatomy of the patient based on the measure of the patient and a corresponding measure of each of the patient anatomy models; and
estimate an irradiation dose for application to the patient by the X-ray system based on the radiation field model and the determined patient anatomy model, and
wherein the at least one processor and memory determines an X-ray distribution by:
determining a dose rate profile based on Monte Carlo simulation;
convolving the dose rate profile with tube current modulation (TCM) and constant tube profiles to generate accumulated z-dimensional dose distributions for each condition;
determining accumulated dose distributions under TCM and constant tube current conditions;
overlaying the accumulated dose distributions with patient organ distributions identified in the patient anatomy models;

determining a regional dose index for organs to account for a local dose field; and multiplying the dose index with volume computed tomography dose index ($CTDI_{vol}$)-normalized organ dose coefficients under constant tube current to approximate organ dose for TCM computed tomography examination.

16. The system of claim 15, wherein the database of patient anatomy models includes patient anatomy models of differing ages, sizes, and genders.

17. The system of claim 15, wherein the at least one computing device is configured to:
receive image data of a plurality of patients;
identify internal structures of the patients based on the image data; and
generate the patient anatomy models based on the identified internal structures.

18. The system of claim 17, wherein the image data is computed tomography (CT) image data.

* * * * *